United States Patent [19]

Rosenstatter

[11] Patent Number: 4,619,009
[45] Date of Patent: Oct. 28, 1986

[54] TOOTH CLEANING APPARATUS

[75] Inventor: Otto Rosenstatter, Seeham, Austria

[73] Assignee: Durr-Dental GmbH & Co. KG, Bietigheim, Fed. Rep. of Germany

[21] Appl. No.: 644,730

[22] PCT Filed: Dec. 23, 1983

[86] PCT No.: PCT/EP83/00347
§ 371 Date: Aug. 23, 1984
§ 102(e) Date: Aug. 23, 1984

[87] PCT Pub. No.: WO84/02453
PCT Pub. Date: Jul. 5, 1984

[30] Foreign Application Priority Data

Dec. 24, 1982 [AT] Austria .............................. 4683/82
Jul. 28, 1983 [AT] Austria .............................. 2752/83

[51] Int. Cl.$^4$ .............................................. A46B 13/04
[52] U.S. Cl. ............................................................. 15/29
[58] Field of Search ................. 15/28, 29, 23, 24, 180; 433/131, 132, 99

[56] References Cited

U.S. PATENT DOCUMENTS

| | | | |
|---|---|---|---|
| 1,848,864 | 3/1932 | Andis | 15/28 |
| 1,896,731 | 2/1933 | Lippett | 15/28 |
| 2,738,528 | 3/1956 | Fridge, Sr. | 15/29 Y |
| 2,933,747 | 4/1960 | Higdon | 15/29 |
| 3,034,376 | 5/1962 | Gonzales | 15/23 |
| 3,195,537 | 7/1965 | Blasi | 15/29 |
| 3,220,039 | 11/1965 | Dayton et al. | 15/28 |
| 3,389,468 | 6/1968 | Lewis et al. | 15/29 |
| 3,629,944 | 12/1971 | Avakoff | 15/28 |
| 3,939,599 | 2/1976 | Henry et al. | 15/28 |
| 3,977,084 | 8/1976 | Sloan | 15/29 |
| 4,089,079 | 5/1978 | Nicholson | 15/29 |

FOREIGN PATENT DOCUMENTS

| | | | |
|---|---|---|---|
| 643312 | 7/1962 | Italy | 15/29 |
| 477799 | 1/1938 | United Kingdom | 15/28 |

Primary Examiner—Edward L. Roberts
Attorney, Agent, or Firm—Robert E. Burns; Emmanuel J. Lobato; Bruce L. Adams

[57] ABSTRACT

Tooth cleaning apparatus comprises a drive and grip part and a brush part removably attached to the drive and grip part. The drive and grip part comprises a cylindrical casing housing an electric motor. The brush part comprises an elongate shank portion which is coaxial with the drive and grip part and is removably attached at its inner end to the cylindrical casing. At its outer end the shank portion has a bearing for a removable brush rotatable about an axis perpendicular to the shank portion. A drive shaft rotatable in the shank portion is connectable at one end with the motor and at the other end has gear teeth meshing with gear teeth on the brush. One or more tubes extending through the shank portion supply fluid to the vicinity of the brush.

13 Claims, 13 Drawing Figures

TOOTH CLEANING APPARATUS

DESCRIPTION

The invention relates to a tooth cleaning apparatus with electric drive, with a drive—and grip part and with a brush part which carries interchangeable brushes moved by the drive and to which a fluid can be supplied through a fluid conduit opening in the region of the bristles. Many tooth cleaning apparatus in the form of electrically driven mechanically movable toothbrushes and fluid supply devices are known.

Under the name "Electric Toothbrush" there is on the one hand a brush system swinging about an axis with a back and forth movement of the brush like the normal hand toothbrush. On the other hand there is a cylindrical brush rotating about an axis with, and having bristles extending radially from, the brush carrier (U.S. Pat. No. 3,739,416, U.S. Pat. No. 3,829,922), which however does not generate any proper movement of the bristles on the teeth and gums. Further there is a rotating brush in which the bristles are arranged in a ring essentially parallel to the axis whereby the ends of the bristles end in a corresponding surface of rotation essentially normal to the axis and work with the front ends ( GB - OS No. 2,008,398 A). Details which are necessary to achieve a practical realization are not given by these publications. An older similarily working hand apparatus according to U.S. Pat. No. 2,252,251 with pressure drive has a driven rotating cleaning body of elastic material but is however, on account of the pressure drive and the lack of bristles not suitable for practical application. An apparatus with a flexible shaft according to U.S. Pat. No. 3,822,432 has a similar dry rotating rubber cleaning head with which especially inaccessible regions of the teeth and gums could not be reached. For dental handpieces there are attachments with rotating brushes and resilient bodies as for example according to U.S. Pat. No. 2,093,007, which, however, are not designed and suitable for daily toothcleaning by the users themselves.

On the other hand there are tooth cleaning apparatuses working with a relatively sharp, usually pulsed, water stream especially for the cleaning of spaces between the teeth and the massage of the gums.

Mechanically movable toothbrushes have also been combined with cleaning apparatuses working with a water stream either with two separate hand apparatus or with one hand apparatus on which the toothbrush or mouth-rinsing nozzle can be attached, whereby corresponding precautions for safe operation are to be taken (U.S. Pat. No. 4,141,352, DE-AS No. 21 09 005, DE-AS No. 21 09 006, GB- OS No. 2 071 498 A). These apparatuses are very expensive in construction and above all are impracticable in operation because for toothcleaning a change of the apparatus or change of the attachment is required.

With back and forth moving or swinging toothbrushes a fluid supply has been incorporated in the hand apparatus or the brushhead (U.S. Pat. No. 3,273,189, DE-OS No. 31 19 338 Al). These systems have found no acceptance in practice presumably because the back and forth moving toothbrush has not achieved the desired good cleaning effect and because the fluid supply was unfavorable. For rotating dental handpiece in particular an angle piece fluid supply from outside to the inclined working surface of the workpiece is known from AT-PS No. 23 99 58. Such a handpiece equipped with bevel-gear drive and ball bearings is too expensive and too heavy for daily self-toothcleaning. Also suitable drive possibilities are lacking in the household and the tools are unsuitable for self-toothcleaning.

An apparatus for feeding and massaging the gums is disclosed in DE-OS No. 29 01 136 in accordance with which a massage tool of rubber is oscillated by a wobble disc and fluid is led from the handle part through a central conduit in the rotary drive to the outer region of the massage tool. The fluid conduit serves in this design in the entire region of the cleaning part as a bearing for the drive shaft whereby the two couplings (fluid and drive coupling) are provided directly next to one another in the region of the mechanical coupling between the drive part and the cleaning part. If the fluid coupling leaks, the drive coupling also immediately becomes wet as no special separation is provided. Moreover the cleaning tool formed with a slim shank is very expensive and cannot be produced as a cheap throw-away part.

If one is to conceive toothcleaning apparatus corresponding to practical needs, a number of points of view must be taken into account. The invention departs from the above-mentioned state of the art and claims 1 and 2 are in particular formulated with reference to DE-OS No. 16 57 287. This arrangement and essential parts of the invention are common in that it relates to toothcleaning apparatus with electric drive with a drive and grip part and with a brush part which carries a removable brush driven by the drive and in which fluid is supplied by a fluid conduit opening in the region of the brush. In the known design, the fluid is supplied centrally between the bristles of a back and forth oscillating toothbrush and indeed the nozzle serving as a spray device. It can be provided as a frustoconical jetdirecting mantel of soft elastic material. In contrast with the invention, the drive of the toothbrush is not electromechanical but through an air pressure vibration device.

A similar departure point for the invention is also the toothcleaning apparatus according to DE-OS No. 31 19 338 in which a conventional electrical toothbrush with oscillating drive of the brush part has a fluid conduit connectable with the apparatus holder entering the rear of the brush part and divided in the brush carrier into three channels through which the fluid is sprayed out approximately parallel to the bristles. In the apparatus holder, there are three different media (cleaning fluid, rinsing fluid, mouthwash) which can be fed selectively or according to a predetermined program during use of the toothbrush.

Exhaustive research has determined that the constant swinging movement of the brush is not favorable as impurities in the region of the gums and spaces between the teeth are thereby brushed deeper into the tooth pockets or spaces between the teeth rather than being removed. This leads to inflammation and thereby bleeding of the gums. Accordingly back and forth moving hollow brushes as for example according to GB-PS No. 5 00 517 are not favorable because they also have oscillation of the hollow brush. The same applies to the apparatus according to AT-PS No. 352 864 which works through the use of a crank drive with driven bristles.

According to the cleaning technique considered today as being especially favorable, the bristles of a toothbrush should move with a small continuous circular movement on the surfaces of the teeth. This cleaning technique is difficult to achieve by hand and moreover there is no apparatus available which with suitable construction also makes possible the favorable flushing according to the manner of a mouth spray.

Thus the object of the invention consists essentially in so improving the above-mentioned prior art that in spite of the supply of at least one medium there is attained a unidirectional rotary motion of the brush whereby a simple replacement of the brush part can be retained or enabled respectively so that toothcleaning apparatus of the above-mentioned prior art is improved by more reliable function in its overall cleaning operation and thereby the operation is essentially simplified for the user.

In accordance with the invention, there is now provided the combination of a rotating end toothbrush with a fluid supply. This can in the description for most countries be thereby characterized that in a toothcleaning apparatus with electrically movable interchangeable brushes and a fluid conduit opening in the region of the bristles, the brush is formed as a hollow brush rotating about its axis and with bristles arranged in a ring and engaging the teeth with their ends.

In a description more suitable for other countries the invention can be summarized as follows:

Toothcleaning apparatus with electrical drive with a drive and grip part and a brush part connected as an elongation thereof on the front head of which there is arranged a brush rotating about its axis and driven by the drive which has bristles arranged on a ring-form brush carrier the bristle end tips of which rotate at least in a plane perpendicular to the axis of rotation or a similarly lying concave surface of rotation such as a part-sphere, part-ellipsoid, paraboloid or truncated cone which engage the teeth with the end of the hollow brush and whereby the axis of rotation of the main extent of the drive and grip part is at an angle to that of the brush part in order to reach the difficult regions of the teeth and gums, and whereby the fluid is supplied through the drive and grip part by a fluid conduit of which the discharge opening lies in the cleaning region of the bristles.

Through the combination of the rotating end brush with a fluid supply which can optionally be used alone or together with the toothbrush and a single hand apparatus in contrast to the known proposal of an oscillating toothbrush, makes possible an optimal cleaning of the teeth in that on the one hand the bristle tips themselves by unsuitable operation cannot remain stationary on the surfaces of the teeth to be cleaned, which is a chief disadvantage of the oscillating brush system, but are forceably moved over the tooth surfaces and that optionally at the same time during the rotating toothbrush treatment fluid, either only water or water with a further medium for treatment of the teeth surfaces and the gums, can be supplied, that on the other hand also without the drive of the toothbrush fluid can be supplied either dispersed or in an aimed pulse stream without any part of the toothbrush being interchanged. This optimal action also cannot be achieved with other known motor-driven toothcleaning apparatus with rotating drive shaft (U.S. Pat. No. 2,215,031, AT-PS No. 1 67 438). With the apparatus according to U.S. Pat. No. 2,215,031 several clusters of bristles are simultaneously driven in rotation one behind another whereby however the action of the entire arrangement can scarcely be distinguished from the above-mentioned oscillating hollow brushes as the circumferential movement of adjacent bunches is directly opposite. Also the rotating brushes of AT-PS No. 1 67 438 is essentially unfavorable with respect to the cleaning action as here the bristles project radially from the bristle carrier. The especially favorable cleaning action given through the simultaneous use of water or a special cleaning fluid in the working region of rotating bristles can also not be realized with the known proposal (AT-PS No. 348 660, EP-PS No. 25 456) because these provide an oscillating brush part which is interchangeable with a part with a spray nozzle through which the cleaning fluid is supplied. Hence with this apparatus either rinsing or brushing of the teeth is possible, however not both at the same time. Rinsing with simultaneous handbrushing is shown in AT-PS No. 354 616 which shows a toothbrush with a water conduit connection. However here the desired circular brush movement must be effected by hand which, however, is not possible in difficultly accessible regions.

For the realization of toothcleaning apparatus in accordance with the present invention there are different possibilities according to whether the fluid supply is to be in the center of the rotating brush or to the outside, or whether the entire brush part is to be made interchangeable so that one and the same drive and grip part can be used by several persons without the danger of transmitting germs or whether it is desired to have a simpler one-person toothcleaning apparatus only with interchangeable brushes and if desired interchangeable fluid nozzles which however can both be simultaneously be driven.

In one development of the invention, the fluid conduit can have at least one discharge nozzle outside the bristles adjacent the rotating hollow brush as is similarly known for oscillating toothbrushes. Then in the inner conception of the drive a central inlet is not required and the nozzles can be formed more freely according to different requirements. According to further especially advantageous embodiments of the invention the fluid conduit can be led into the central space of the bristles and the brush carrier of the hollow brush is formed as a bushing and the fluid conduit opens with its forward end coaxially with the bushing and into the space surrounded by the bristles. Then the cleaning fluid is supplied centrally of the treatment and can be well contained by the central drive of the bristles. The conduit lead-in can contribute to the centering and provides a neat construction.

For supplying different treating fluids at least two fluid conduits can be provided which allow common discharge of the fluids at least in the outlet region. Thus the apparatus can be adapted for the most diverse cleaning and treating requirements merely through the addition of further media. Thereby the main fluid conduit can be surrounded by an annular space in which at least one further conduit for supplying a further medium opens. Thus a mixing occurs directly before the treatment and a reactionable mixture can be brought together directly in the treating zone. The supply of the further media can be effected under pressure when that appears suitable whereby such pressure can be produced in the apparatus or outside the apparatus. The supply of the further medium can however according to a further embodiment be effected through injection action of the main fluid stream. Then further pressure sources or valves for the supply and pressurizing are not required. A very easily produced and functionally efficient solution to obtaining a rotating hollow brush with fluid supply can especially be achieved in the manner that between the outer surface of the forward end of the fluid conduct inserted in the bushing and the innerwall of the bushing there is formed an annular space which forms a connecting channel to the inner region of the bearing bore in which at least one further conduit enters for supplying a medium. With all solutions in which the fluid is supplied centrally, there is the advantage that the tooth surfaces, the tooth pockets and the spaces between the teeth can be quickly and effectively cleaned whereby the circle of bristles helps to retain the supplied fluid longer in the operation site. When additionally at least one further medium is supplied in the region of the discharge of the first fluid conduit, a mixing, for example to produce a reaction mixture of the two media, can be effected as close as possible to the place of operation. By mixing in the inner region of the bushing, the mixing occurs only the length of the bushing from the circle of bristles.

A rotating hollow brush with a bevel drive is to be inferred from GB-OS No. 2 008 939 A. However the brush part is not arranged detachably on the drive part and there is no fluid supply with which there would be a particular problem of construction. In departure therefrom and another solution the invention provides for apparatus with and without fluid supply that the driveable hollow brush rotating on its axis is carried on a brush part that is removable from the drive and grip part and between the drive and grip part and the brush part there is provided a releasable coupling means which comprises at least one coupling in the rotating drive and locking part for retention. Such apparatus can then be used in a multi-person household without danger of transmission of germs and the brush part can be produced as an economical mass-produced part. The locking coupling can advantageously be formed in the manner that the brush part is formed with locking hooks received in recesses in the drive and grip part which grip behind locking webs which are formed on a locking and deformable part which is formed as a thin wall end portion of the drive and grip part and which has marked pressure regions that upon downward pressure of the pressure regions, the locking webs of the deformable region are expanded. Such a coupling can easily and economically be produced by injection molding and is functionally efficient in continous use.

An especially favorable solution for the detachable coupling of the rotating hollow brush and the favorable bearing of the drive shaft as well as the brush part is that the rotating and motor driven drive shaft in the drive and grip part is supported in a hollow shaft which extends from the drive and grip part and on its forward end carries a socket which has a bevel ring gear which meshes with a bevel gear ring on the brush carrier which is supported in the brush part at an angle to the direction of its main extent. Such construction, which is also advantageous for a multi-person toothbrush without fluid supply, permits a very simple form of the brush part and of the bearing of the brush carrier so that economical mass-produced parts can be produced and there is thus provided a very simple easily produced and efficient solution to obtaining a rotating hollow brush for several persons with a base apparatus whereby the separation of the drive is effected by changing the head. Thereby the removable brush carrier is advantageously elongate with at least the entire portion of the cleaning apparatus that is to be inserted in the mouth. Advantageously it has a channel passing through the shaft and a thin wall, the external shape of which is essentially cylindrical, and in the region of the connection with the drive and grip parts expands conically. When it is desired to provide such brush part with a fluid conduit, this and if necessary, a further conduit is allowed to run essentially parallel to the central channel for the shaft of the drive and grip part whereby these are preferably set in the wall of the main channel. Thereby the section of the fluid conduit in the brush part is connected by a plug-in coupling with the section of the fluid conduit in the drive and grip part. For multiple conduits this is formed as a multiple coupling. In the region of the coupling the fluid conduit or fluid conduits are set back from the end face of the brush part and end in an enlargement for reception of the coupling part provided with a seal in the drive and grip part. Thus like brush parts it can be used for toothbrushes with and without fluid supply in order to rationalize mass production. The drive coupling on the one hand and the locking parts and fluid couplings on the other hand are spaced from one another and thereby reciprocally free of influence and simply and effectively sealable.

For feeding the fluid conduit, an external table or wall apparatus in the nature of a mouth spray or pump or a pump in the drive and grip part can be provided. A pump in the drive and grip part is preferred with the drive shaft of the rotating drive coupled or couplable and can be formed as a hose pump.

An especially simple construction of the toothcleaning apparatus in accordance with the invention results from the bearing of the bristle carrier. Here too it is provided in a preferred embodiment that joined to the bevel gear of the brush carrier there is a reduced bearing section which is received in the bearing bore of the head of the brush carrier and is secured through a radially insertable slip lock. Such a bearing is suitably and in accordance with the invention provided for toothcleaning apparatus with and without fluid supply and also for toothcleaning apparatus with an entire replaceable brush part or with a brush part fast with the drive and grip part. It can be formed as a one-piece element with the replaceable brush which is then formed as an inexpensive throw-away part if the material of the bevel gear is sufficiently durable for the life span of the brush. An especially suitable form is that the brush carrier is divided into a bearing and bevel gear part with bevel gear teeth and a brush carrier proper which are rotationally fixed to one another by a plug-in connection. Then the bevel gear tooth part can be formed with the durability required for the small teeth and need not take into account the requirements of securing the bristles which under circumstances differ from the requirements for the drive but can form the brush carrier according to the requirements of optimal production and securing of the bristles. The cost of production of the replaceable brushes is thereby further decreased.

The brush carier can thereby be formed as an essentially plane disc with a central opening, on which the bristles are secure. Also such a toothbrush could be used for cleaning apparatus without fluid supply and with fluid supply. That is true also for the brush formed with an integral bevel gear.

The sleeve for fixing the disc can have a truncated axial extension which is provided with at least one radially yieldable projection which engages in at least one recess in the corresponding axial surface of the disc. Advantageously the projection can be formed as an elastic ring received in a groove in the extension. In order to ease removal, the outer end face of the bristle carrying disc can for example be profiled with a circumferential groove or the like.

Of particular note is also the form of the brush as such and in particular the selection of the bristles and the form of the bristle tips. These are rounded for a gentle cleaning and massage. In accordance with invention, it is especially advantageous for the tips of the bristles to end at different distances from the brush carrier, because they can conform to the anatomy especially well, and above all, permit reaching tooth pockets and spaces between the teeth better. The ends can lie in the most different surfaces mentioned above. An especially good cleaning effect can be obtained when at least two circles of brushes are arranged on the sleeve, the bristle carrier or the disc whereby the bristles of at least one outer ring extend beyond those of at least one inner ring so that there is a stepped brush in which the bristles however support one another. The distance the outer bristles extend beyond the inner bristles can for example be half the length of the bristles of the inner circle. The bristles are advantageously inclined outwardly at an angle between 5° and 30°, preferably between 15° and 20° to the axis of rotation of the hollow brush or sleeve access. Thus the tooth angles can be cleaned by the inner bristles and it yields a good reinforcing and nevertheless an individual cleaning effect also to the places which are difficult to reach. An especially good cleaning effect is obtained with the brush of the aforsaid kind between 2500 and 300 revolutions per minute, preferably between 1000 and 500 revolutions per minute when the inner diameter of the hollow brush is between 5 and 10 mm. A lower speed of revolution improves the penetration of the bristles into the spaces between the teeth while a higher revolution speed improves the cleaning efficiency. A good usable compromise thus lies in the given preferred range. The brushes and their drive particulars are well suited for cleaning without fluid and with fluid.

Further details and developments of the invention are given in the following description with reference to the drawings whereby the invention is however not limited to the illustrated embodiments, but different variants are permitted and whereby moreover the individual characteristics need not all be present in combination but also individually for advantageous solutions in apparatus of other kinds. The invention lies essentially in three aspects which offer special advantages, singly as also in possible combination with one another and represent invention: (1) Combination of a rotating hollow brush working with its end face with the supply of a fluid, with the possibility of the fluid supply from outside or in the center and with the fluid conduit discharge essentially parallel to the bristles, the fluid conduit in the brush part extending longitudinally and with the possibility for several fluids which can be used singly or together. (2). Construction of a replaceable brush head with mechanical coupling in the region of the bevel gear drive and if necessary coupling of the fluid conduit in the connecting region. The construction of the interchangeable brush part is thereby simplified and a firm bearing of the drive shaft and a simpler, more reliable mechanical drive is achieved, despite the separation. (3). Construction of the rotating brush with easily interchangeable brush carrier, if necessary, in spite of the supplying of a fluid in the center and arrangement of the bristle ends in different planes or surfaces as well as angles and materials whereby the bristles are arranged on the bristle carrier endwise as a hollow cylinder.

Embodiments of the invention will be described by way of example below with reference to the drawing.

Figure 1:
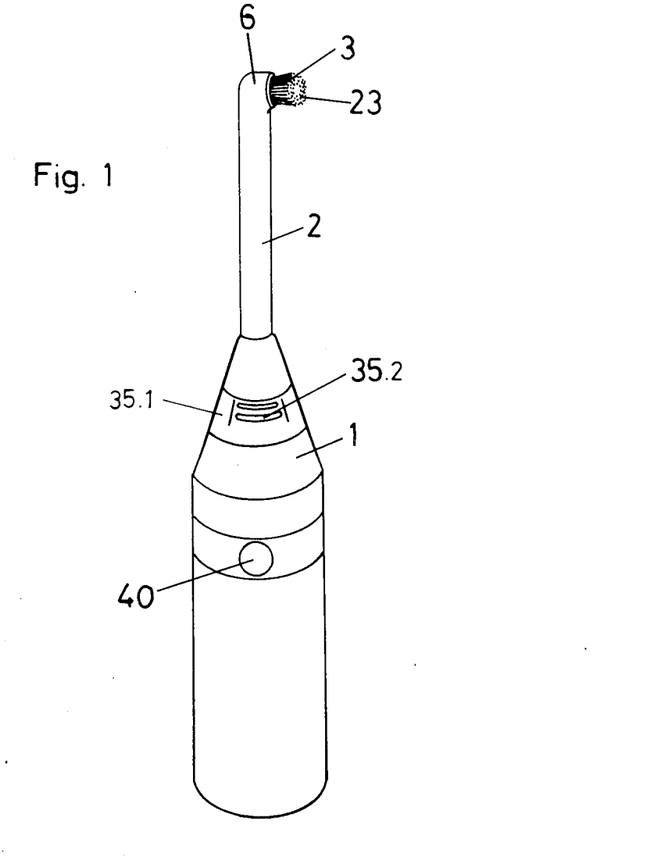
FIG. 1—The elevation of a tooth cleaning apparatus.
Figure 5:
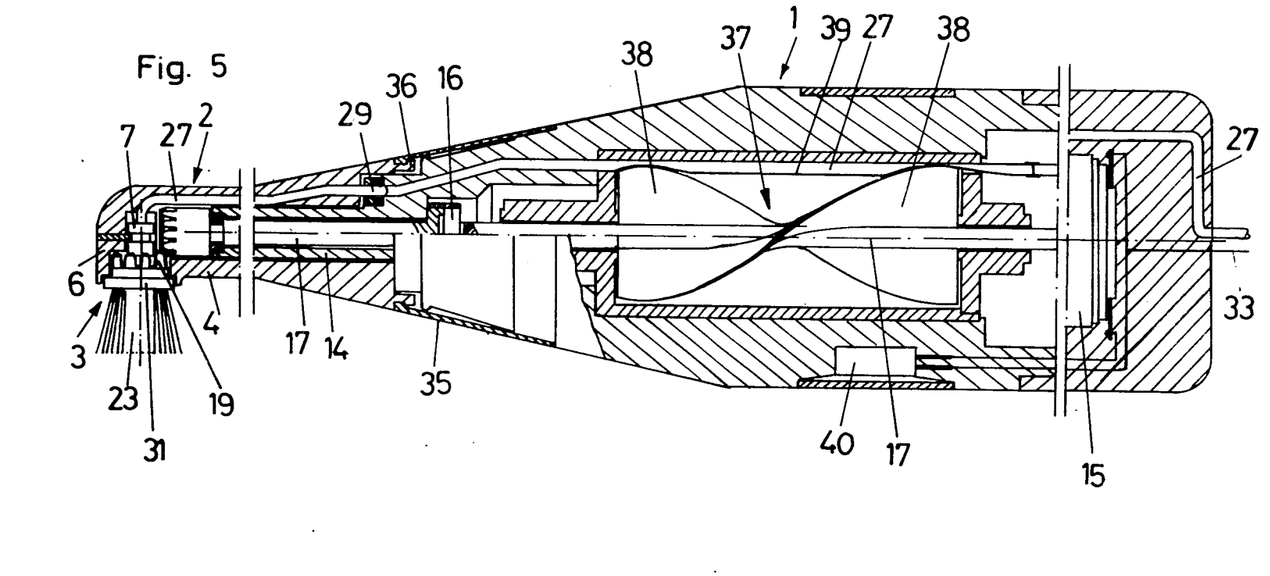
FIG. 5—A longitudinal section through a tooth cleaning apparatus of a second embodiment with fluid delivery conduit to the brush head.

FIG. 1 shows an outside view of a tooth cleaning apparatus which corresponds essentially to all of the following embodiments. Such tooth cleaning apparatus has a drive and grip part 1 and in extension thereof, a connected brush part 2 on which a rotating hollow brush 3 is arranged on a brush head 6 at an angle to the longitudinal direction of the drive and grip part 1 and the brush part 2. An electric drive motor 15 (FIGS. 2 and 5) is arranged in the drive and grip part 1. It could be supplied with current by a rechargeable battery built in to the grip part or an electrical connecting cable (FIG. 5). For the purpose of coupling and uncoupling the mechanical coupling and separation of the brush part 2, the forward region of the drive and grip part is made thin-walled and deformable as a lock and deformable part 35.1 with marked pressure regions 35.2. A switch is preferably protected by a cover of 40, for example, of rubber.

Figure 2:
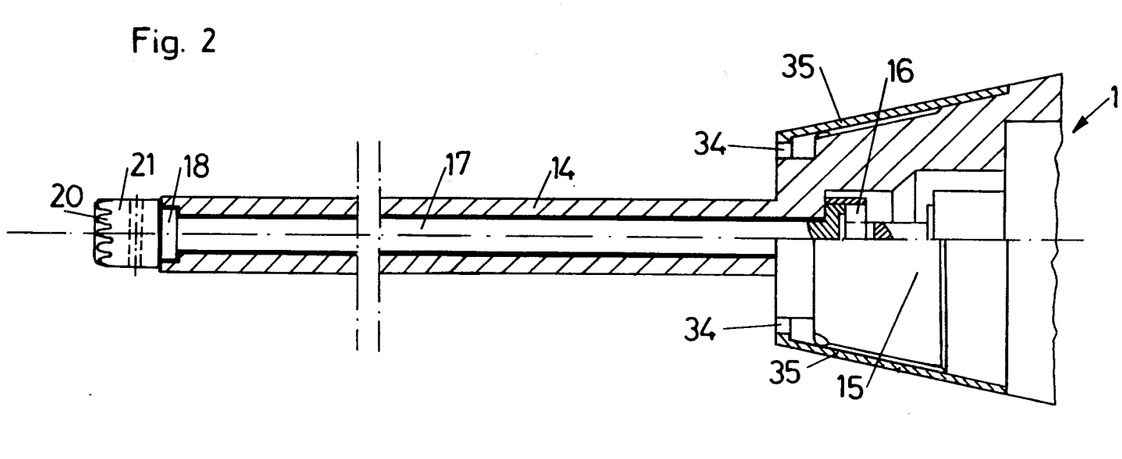
FIG. 2—A longitudinal section through the forward part of the drive and grip part with the enclosed shaft, whereby the lower half in the drive and grip part relative to the housing and lock and deformable part cut relative to inner-lying part of the motor coupling and cover is shown in elevation.

FIG. 2 shows the mechanical construction for the rotating drive of the hollow brush 3 supported on an attachable brush part 2.

Figure 4:
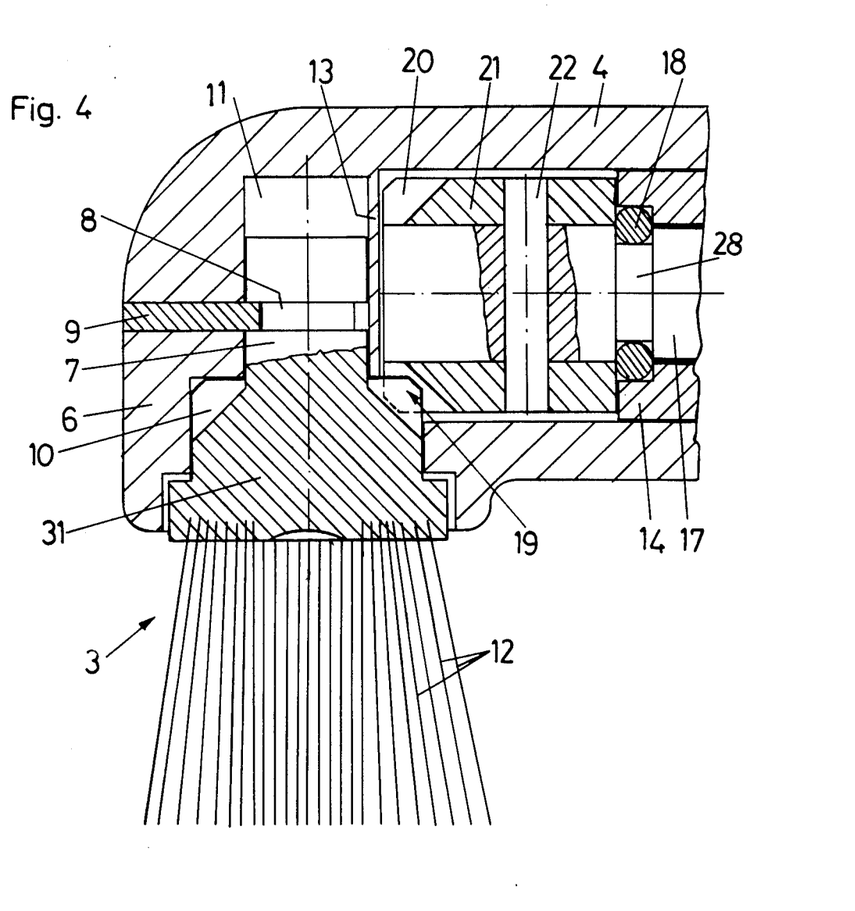
FIG. 4—An enlarged partial section through the head of the brush part, whereby this corresponds to the assembled condition and to the illustrations of FIGS. 2 and 3.

From the drive and grip part 1 there protrudes a hollow shaft 14 (FIG. 2 and 5) in which a drive shaft 17 connected with the motor 15 by a coupling 16 is rotably supported. Of the forward end of the drive shaft 17 projecting out of the shaft 14 it is provided with a sleeve 21 having a bevel gear 20, which is secured by means by a pin 22 extending diametrally through the drive shaft 17 (FIG. 4). Between the sleeve 21 and the forward end of the shaft 14, there is slip and sealing ring 18 set in an angular groove 28 of the drive shaft 17.

Figure 3:
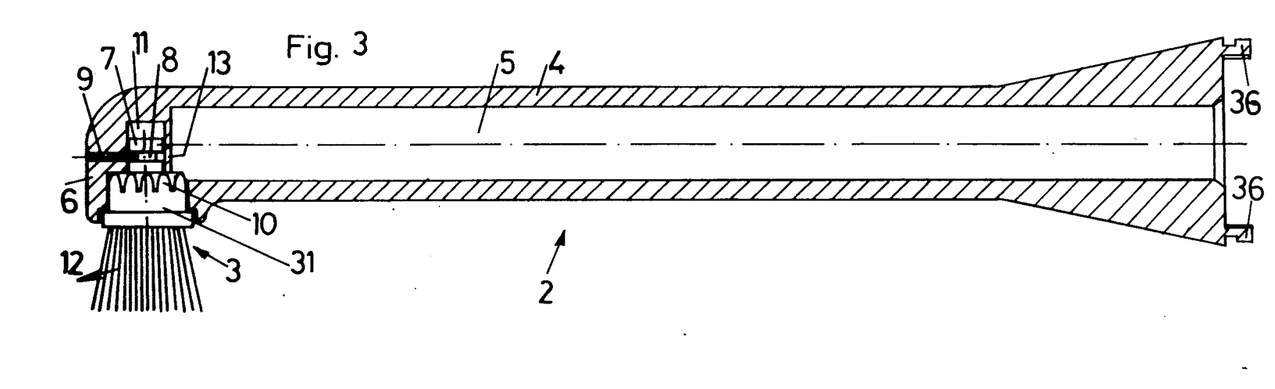
FIG. 3—A longitudinal section through a brush part attachable on the shaft.

FIG. 3 shows in longitudinal section a brush part 2 attachable on the shaft 14. The brush part 2 has a coaxial receiving channel 5. The wall 4 of the brush part 2 is formed cylindrical over a great part of its length and expands conically to join the drive and grip part 1. For the formlocking and rotation fast connection with the drive and grip part 1 there are provided locking hooks 36 which are insertable in recesses 34 of the drive and grip part 1 and are there gripped by resiliantly arranged locking webs 35. The locking webs 35 are formed on a thin wall forward conical lock-and deformable part 35.1 and are slightly expandable by lateral pressure on the marked pressure regions 35.2 to free the locking hooks 36 of the brush part 2 so that it can be drawn from the shaft 14.

On the free end of the brush part 2 its head 6 is set at an angle of about 90° to the direction of the main part and provided with a hollow brush 3. As hollow brush will be understood that the bristles 12 are arranged ring-or wreath form on a bristle carrier from which they project and leave a central space 23 free. Here the bristle carrier 31 is formed as a sleeve 32. The brush is thus formed as a rotating brush rotating about its axis with the end face directed toward the teeth in which the bristle tips end in a plane perpendicular to the axis of rotation or somewhat similarly lying concave surface of rotation such as part-sphere, part-ellipsoid, paraboloid, truncated cone. Thereby as will be further pointed out below, the bristles can end also in several planes or surfaces. Their ends are suitably formed for the treatment so that they make possible good cleaning but produce no injury in particular to the gingiva, thus are preferably rounded.

To receive the hollow brush 3 the head 6 is preferably provided with a bearing bore 11 which is perpendicular to the receiving channel 5. The two pocket bores (receiving channel 5, bearing bore 11) do not however pass fully into one another but are to a great extent separated by a web 13. The bearing bore 11 thereby forms an outer bearing for a reduced bearing section 7 of the brush carrier which in this embodiment is formed as the bristle carrier 31. It is provided with a bevel gear 10 the teeth of which engage the bevel gear teeth 20 of the sleeve 21. To enable this engagement and thereby the formation of the bevel gear drive 19 the enlarged bearing bore 11 to receive the tooth circled 10 is in this region provided with an opening into the receiving channel 5. The bearing section 7 carries a ring groove 8 into which a slide lock 9 anchored in the hub 8 is pushed in. The sleeve 32 of the hollow brush 3 is thereby easily interchangeably held axially non-slidable in the head 6. A such or similar bearing of the brush carrier with bevel gearing and engagement in the bevel gear of the drive is common in all of the illustrated embodiments. By way of example, the axis rotation is here at an angle of about 90° to one another. However, according to the form of the brush and other structural conditions of the apparatus, an angle differing from 90° can be selected.

Figure 6:
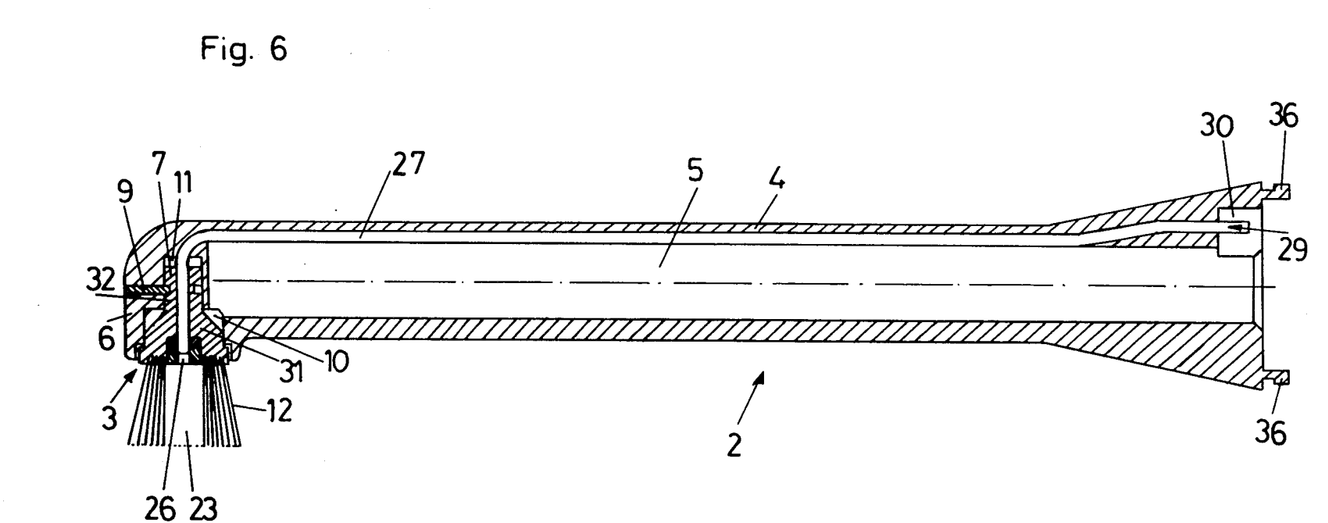
FIG. 6—A longitudinal section through the brush part of the apparatus according to FIG. 5.
Figure 7:
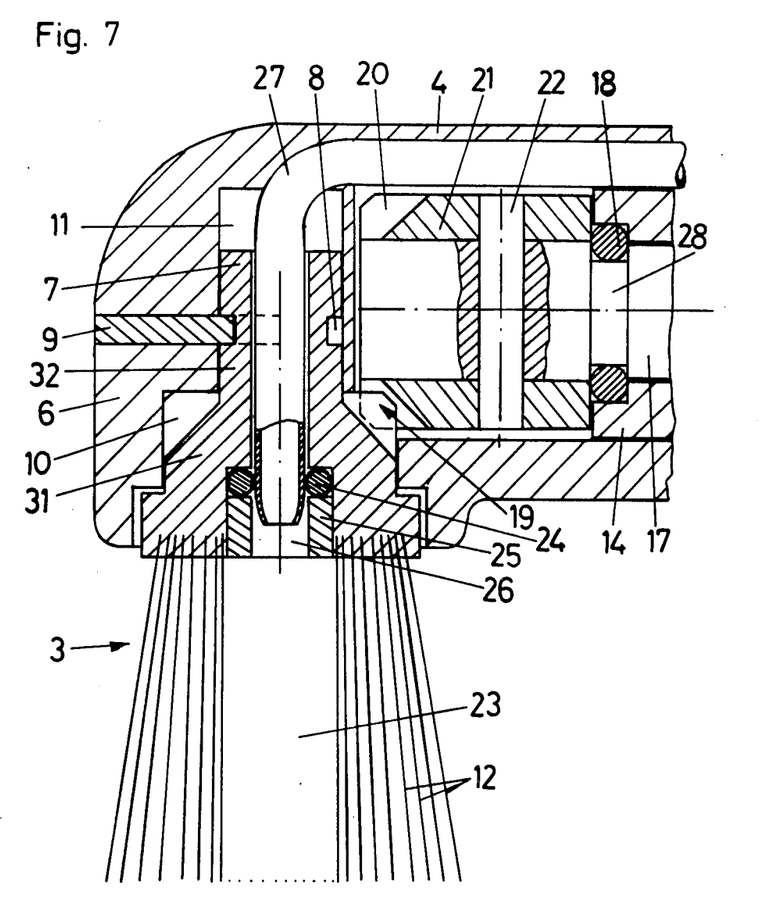
FIG. 7—An enlarged longitudinal section through the head of the brush part of the embodiment according to FIGS. 5 and 6 however in assembled condition.

The embodiment illustrated in the FIGS. 5–7 shows additionally supplying of fluid in the cleaning region of the bristles and indeed here in preferred form in the bristle middle space 23 of the hollow brush 3 and thus directly in the area of application.

Compared with the embodiment according to FIG. 2–4 only limited supplements but no basic alteration is required in the brush part 2. The brush carrier is here also formed as the direct bristle carrier and represents together with the bearing section 7 a sleeve 32 through which the bent end section of a fluid conduit 27 extends axially into the brush middle space 23. The bristle carrier 31 has therefore an enlarged outlet opening 26 in which a slip and sealing ring 24 surrounds the end of the fluid conduit 27 and is held by an insert sleeve 25. The fluid conduit 27 can be in particular a tube of rubber or suitable plastic, however also a thin metal tube. In this embodiment the fluid conduit is made continuous and opens axially inside the bearing bore 11 into the enlarged outlet opening 26. From the bearing bore 11 the fluid conduit 27 extends continuously along the receiving channel parallel thereto in the wall 4 in which it is set and ends in an enlargement 30 in the junction region of the brush part 2 which lies inside the end face. In the enlargement 30 the end of the fluid conduit projects as a fluid coupling 29 as seen in FIG. 6 so that the conduit end can be plugged into a coupling sealing ring arranged in a housing recess in the head of the drive and grip part 1 as can be seen in FIG. 5. The fluid conduit 27 extends further in all embodiments with fluid supply through the drive and grip part and can there be formed in different manners. According to FIG. 5 it enters the rear end of the drive and grip part 1 and extends lengthwise through the same. It can be fed from outside or supply means for the fluid can be provided internally in the drive.

The fluid coupling 29 is separated by approximately by the length of shaft 14 from the drive coupling, the bevel gear drive 19 and is arranged in the vicinity of the mechanical coupling through the locking parts, locking web 35 and locking hooks 36. Through the recessing of the conduit ends behind the end face and as the construction of the brush part 2 according to FIG. 6 otherwise corresponds fully to that of FIG. 3, the brush part with the fluid supply conduit 27 can also be put on the drive and grip part according to FIG. 2 in which no fluid supply means is provided. The entire length of the brush part is at least as great as the length inserted in the mouth in order to reach the rearmost teeth and not allow the drive and grip part to come into contact with the lips and mucous membrane.

The fluid supply can be realized in different ways. According to FIG. 5 a drive and grip part 1 is provided with fluid supply with a hose pump 37 which has two helicoidal vanes 38 on the drive shaft. The vanes 38 squeeze the fluid conduit 27 continuously from the rear to the front so that fluid drawn from outside is passed on to the hollow brush 3. In order to protect the fluid conduit 27, there is provided a separating or protecting layer 39. In the drive and grip part 1 in connection with the hose pump 37 there is arranged the electrical drive motor 15 which directly drives the drive shaft 17 carrying the hose pump 37. However in FIG. 5 the region accomodating the motor 15 as well as brush part 2 has been shortened to save space and contains no constructive details. The end of the hose conduit 27 extending out of the drive and grip part 1 can be dipped into a cleaning fluid container out of which the fluid is drawn through the self-priming hose pump 37. However a resevoir can be provided in the drive and grip part 1. As already mentioned the electrical supply can be a rechargeable battery so that the electrical cord 33 is not necessary. When no continual supply of the fluid is desired, the pump can be otherwise formed and can be on and off couplable or can be wholly omitted and replaced by an external pump.

Figure 8:
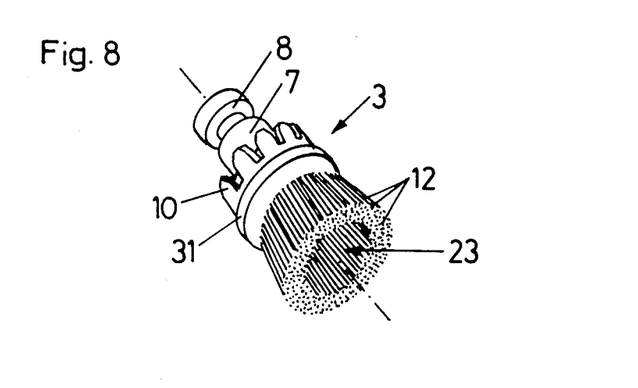
FIG. 8—A hollow brush in perspective view.

FIG. 8 is a perspective view of a hollow brush with a brush carrier 31 and bevel gear 10 as well as bearing section 7 and ring groove 8 whereby the bristles 12 are arranged endwise in a circle around the brush middle space 23 directly on the brush carrier 31 corresponding to the embodiments herefore described whereby the inner space of the brush carrier can be solid as shown in FIG. 3 and 4 or hollow as shown in FIGS. 5, 6 and 7.

Figure 9:
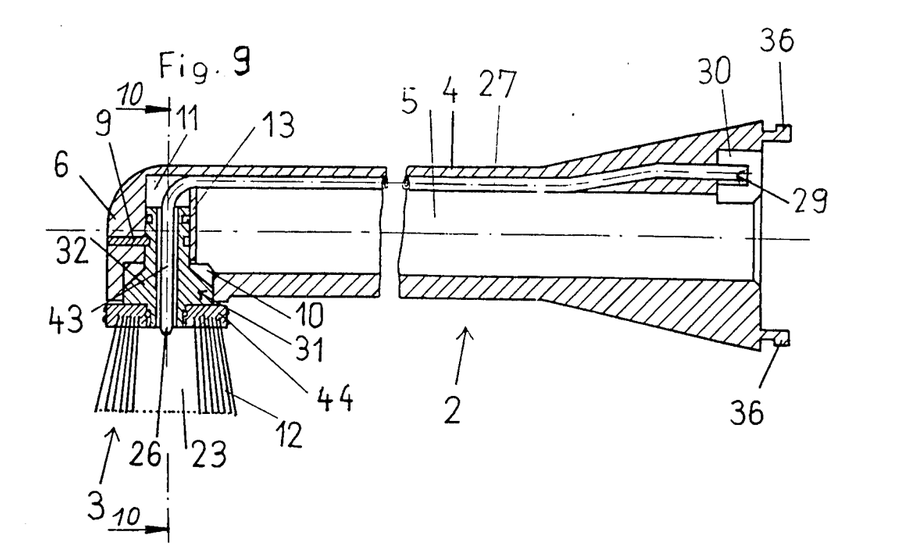
FIG. 9—A longitudinal section through a brush part of a further embodiment.
Figure 10:
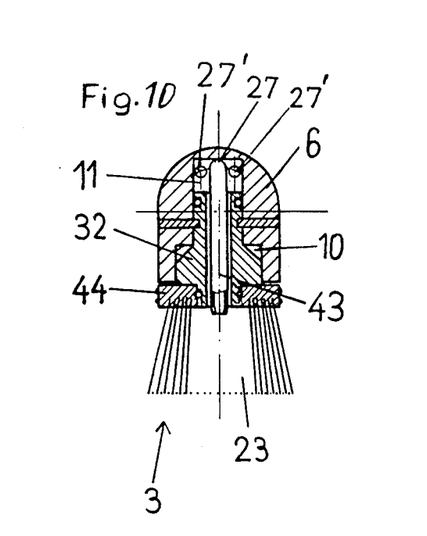
FIG. 10—An enlarged cross section along the line 10—10 in FIG. 9.
Figure 11:
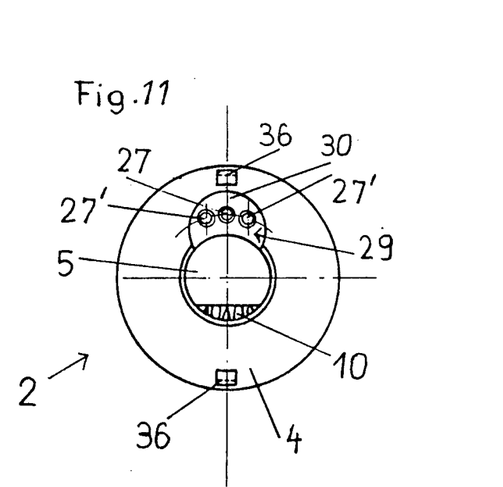
FIG. 11—An end view of the brush part according to FIGS. 9 and 10 in the region of the mechanical coupling and the fluid coupling.

In the embodiment of FIGS. 9–11 fluid supply is likewise provided similarly as herefore described. However, as seen especially from FIGS. 10 and 11 there are two further conduits 27¹ parallel to the fluid conduit 27 in the wall 4 of the brush part 2 which open through the web 13 into the bottom region of the bearing bore 11. Media supplied through the conduits 27¹ pass out of the bottom region of the bearing bore 11 through an annular space 42 coaxial with the end section 43 of the fluid conduit 27 through the sleeve 32 into the bristle middle space 23. The mixing of a fluid out of the conduit 27 with medium out of the conduit 27¹ is thus first possible in the bristle middle space so that a possible reaction mixing is first produced in the area of application. The conduits can be fed with different fluids singly or together, wherefore in the drive and grip part 1 corresponding provisions are made through valves and/or supply containers and substitution possibilities for the materials to be mixed up. In the head 6 a mixing space is provided for the two conduits 27¹.

Figure 12:
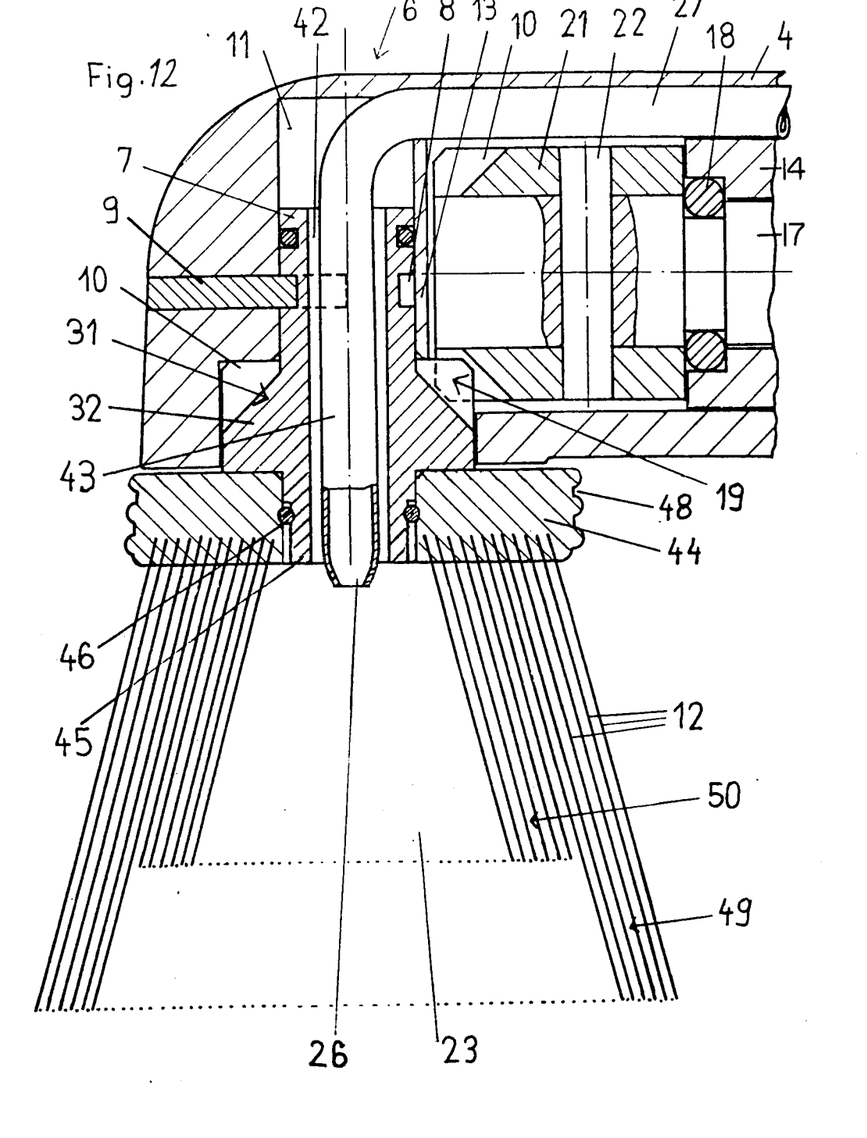
FIG. 12—A longitudinal section through a brush head similar to FIG. 7 but with stepped brush and some variants.
Figure 13:
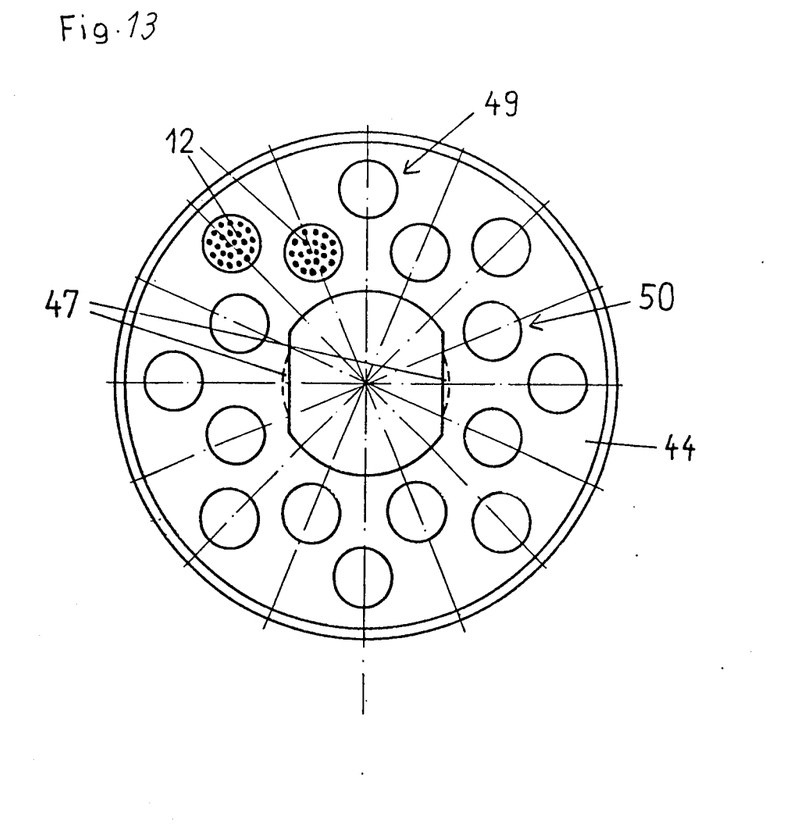
FIG. 13—Plan view of a bristle disc of the embodiment according to FIG. 12.

The embodiment of FIG. 9–11 shows a further variant. It was previously shown that the bristles 12 are fastened directly on the brush carrier formed as the bristle carrier 31 and thus the brush carrier is removable through drawing the slide lock 9 and through corresponding insertion is inserted over the fluid conduit 27. Thereby arises the danger of bending and difficulties in insertion. Moreover, a somewhat expensive brush carrier with bearing and gear teeth is required. This is however relatively easily interchangeable. However, to reduce the cost of parts subject to wear as illustrated in the embodiment of FIGS. 9–11 and the variant of FIGS. 11–13, the bristles 12 are set in a disc 44 formed as the brush carrier proper. This is affixed nonrotatably but interchangeably on an extension 45 of the sleeve 32. For a nonrotatable fixing, teeth or as illustrated in FIG. 13 suitable flat surfaces can be provided. For withdrawable axial fixing there can be provided in the inner surfaces of the disc 44 two recesses 47 (FIG. 13) in which projections of the extension 45 formed for example through an elastic clamping ring 46 or a small metal spring ring, engaged. The clamping ring 46 is thereby seated in a circumferencial groove in the extension 45. For easy withdrawing of the disc 44 by pulling on the brush the circumferencial surface thereof is advantageously profiled, for example with circumferencial grooves 48 or the like.

For good efficiency of cleaning without danger of injury and with good accessability to all regions it is advantageous to let the bristles end in different planes perpendicular to the axis of rotation for example two planes or also surfaces of rotation such as part-circle, part ellipsoid, paraboloid or truncated cone. FIG. 12 shows a preferred exemplary development in which the bristles 12 are arranged in two circles 49 and 50 whereby the bristles of the outer circle 49 extend beyond those of the inner circle 50. Through the differnet lengths of the bristles 12 in the two circles 49 and 50, the bristles of the inner circle are stiffer and support the bristles of the outer circle 49 on the rotation of the bristle carrier 31 so as to avoid the twisting of the bristles into a twisted strand which could hinder discharge of the fluid or medium into the bristle middle space 23. If necessary the bristles of the two circles 49, 50 can also be of different materials which are selected, dimensioned and arranged according to the different cleaning and treating problems.

The cleaning apparatus in accordance with invention has adjacently local separation of the drive and fluid coupling 19, 29 and especially simply constructed interchangeable brush part 2 which is provided with a medium supplying hollow brush making possible an especially intensive cleaning.

The brush part 2 is easily changed from the drive part 1 through a fast coupling so that it is usable with the desired hygiene for several persons (family). In tooth cleaning only the interchangeable brush part 2 and not the drive and grip part comes into contact with the mucous membrane; it thus has a certain minimum length, the insertion length. Moreover, each interchangeable brush part 2 is conceived as especially cost favorable as it comprises only a bevel gear drive and an interchangeable bristle disc 44, so that they are suitable for mass production as throwaway parts.

Essential parts of the invention can also be described as follows:

The tooth cleaning apparatus with electric drive has a drive and grip part with a drive motor and if necessary a switch. In its elongation an interchangeable brush part is arranged. Through pressure on the pressure regions of a deformable part the brush part can be removed. The brush part carries on its angled head a hollow brush the bristles of which are arranged endwise on a bristle carrier rotating about its axis. The bristles leave free a central space between the tufts arranged in a circle. The bristle carrier can be formed as a collar on which the bristles are arranged in the form of a wreath and rotatably supported in the head of the brush part with bevel gear teeth which mesh with bevel gear teeth on the end of a drive shaft rotating in a hollow shaft of the drive part whereby the shaft is insertable in a receiving channel of the brush part and the fluid conduit which is set in the wall of the receiving channel for the shaft can with its forward end coaxially penetrate the collar and open in the space surrounded by the bristles, and with its rear end projecting endwise out of the brush part to connect with the supply conduit coming out of the drive part.

I claim:

1. Tooth cleaning apparatus comprising
   a drive and grip part comprising a symmetrical cylindrical casing and a motor housed in said casing, and,
   a brush part removably attached to said drive and grip part comprising a hollow elongate shank portion extending from an end of said casing and having at its outer end a transverse bearing for a rotatable brush, a brush rotatable in said bearing and a drive shaft having at an inner end driving connections with said motor and at an outer end driving connections with said rotatable brush,
   said elongate shank portion and drive shaft being coaxial with said cylindrical, said shank portion having an enlarged inner end portion coaxial with and adjoining said cylindrical casing, diametrically opposite hook portions provided on said enlarged inner end portion of said shank portion and engageable with locking webs formed on a deformable thin wall portion of said cylindrical casing, said thin wall portion of the casing being deformable by lateral pressure applied to selected regions to disengage said hook portions from said webs and thereby release said brush portion from said casing.

2. Tooth cleaning apparatus comprising:

a drive and grip part comprising a symmetrical cylindrical casing and a motor housed in said casing, and a brush part removably attached to said drive and grip part comprising a hollow elongate shank portion extending from an end of said casing and having at its outer end a transverse bearing for a rotatable brush, a brush rotatable in said bearing and a drive shaft having at an inner end driving connections with said motor and at an outer end driving connections with said rotatable brush, said elongate shank portion and drive shaft being coaxial with said cylindrical casing, said brush having a stem portion insertable axially into said bearing at the outer end of said shank portion, and a slide lock slidable in an outer end of said shank portion and engageable with an annular groove in said stem portion of said brush to retain said stem portion releasably in said bearing.

3. Tooth cleaning apparatus comprising:

a drive and grip part comprising a symmetrical cylindrical casing and a motor housing in said casing, and a brush part removably attached to said drive and grip part comprising a hollow elongate shank portion extending from an end of said casing and having at its outer end a transverse bearing for a rotatable brush, a brush rotatable in said bearing and a drive shaft having at an inner end driving connections with said motor and at an outer end driving connections with said rotatable brush, said elongate shank portion and drive shaft being coaxial with said cylindrical casing, and means for supplying fluid to said brush, said fluid supplying means comprising a flexible tube extending out through said hollow shank portion and a helicoidal vane on said drive shaft engaging and squeezing said tube progressively along its length as said shaft rotates to propel fluid through said tube.

4. Tooth cleaning apparatus according to claim 3, further comprising a flexible protective layer interposed between said helocoidal vane and said tube.

5. Tooth cleaning apparatus according to claim 3, in which an end portion of said tube extends externally of said casing for insertion into a fluid container for sucking fluid from said container.

6. Tooth cleaning apparatus comprising:

said brush a drive and grip part comprising a symmetrical cylindrical casing and a motor housed in said casing, and a brush part removably attached to said drive and grip part comprising a hollow elongate shank portion extending from an end of said casing and having at its outer end a transverse bearing for a rotatable brush, a brush rotatable in said bearing and a drive shaft having at an inner end driving connections with said motor and at an outer end driving connections with said rotatable brush, said elongate shank portion and drive shaft being coaxial with said cylindrical casing, and having a hollow stem portion rotatable in said bearing, and means for supplying fluids to said brush comprising first and second tubes extending through said hollow shank portion, said first tube having a bent end portion in said hollow stem portion of said brush with an annular space around said first tube end portion, and said second tube being connected with said annular space, whereby fluids supplied through said first and second tubes respectively mix in the vicinity of said brush.

7. Tooth cleaning apparatus comprising, a drive end grip part comprising a symmetrical cylindrical casing and a motor housed in said casing, and a brush part removably attached to said drive and grip part comprising a hollow elongate shank portion extending from an end of said casing and having at its outer end a transverse bearing for a rotatable brush, a brush rotatable in said bearing and a drive shaft having at an inner end driving connections with said motor and at an outer end driving connections with said rotatable brush, said elongate shank portion and drive shaft being coaxial with said cylindrical casing, said brush comprising a cylindrical body portion having bevel gear teeth thereon, a stem portion extending from one end of said body portion and releasably received in said bearing of said shank portion of said brush part and a central extension extending from the opposite end of said body portion, a flat annular disc surrounding said extension and releasably received thereon and a multiplicity of bristles projecting from said disc in a direction away from said body portion, and means comprising a slide lock engageable with an annular groove in said stem portion for releasably retaining said stem portion in said bearing and means for releasably retaining said disc on said central extension.

8. Tooth cleaning apparatus according to claim 7 in which said bristles comprise an inner ring of shorter bristles and an outer ring of longer bristles.

9. Tooth cleaning apparatus comprising:

a drive and grip part comprising a cylindrical casing and a motor housed in said casing, and a brush part removable attached to said drive and grip part and comprising a hollow elongate shank portion extending from an end of said casing and having at its outer end a transverse bearing for a rotatable brush, a drive shaft rotatable in said shank portion, having driving connection with said motor at its inner end and bevel gear teeth at its outer end, and a brush mounted at the outer end of said shank portion for rotation about an axis at least approximately perpendicular to said shank portion, said brush comprising a cylindrical body portion having bevel gear teeth meshing with said bevel gear teeth on the outer end of said drive shaft, an integral stem portion extending from and one end of said body portion and releasably received in said bearing of said shank portion, and an integral extension extending from the opposite end of said body portion, a flat annular disc surrounding said extension and releasably retained thereon and a multiplicity of bristles projecting from said disc in a direction away from said body portion said stem portion of said brush having an annular groove therein, and, a slide lock slidable in an outer end portion of said shank portion of said brush part and engageable in said annular groove releasably to retain said stem portion of said brush in said bearing.

10. Tooth cleaning apparatus according to claim 9, in which said bristles comprise an inner ring of shorter bristles and an outer ring of longer bristles.

11. Tooth cleaning apparatus according to claim 9, in which an axial passage extends through said body portion, said stem portion and said extension of said brush and in which means is provided for delivering fluid through said axial passage.

12. Tooth cleaning apparatus according to claim 11, in which said fluid delivery means comprises a tube extending through said shank portion of said brush part and having a bent outer end portion in said axial passage of said brush.

13. Tooth cleaning apparatus according to claim 11, in which said fluid delivery means comprises a first tube extending through said shank portion of said brush part and having a bent outer end portion in said axial passage of said brush with an annular space around said bent end portion, and a second tube extending through said shank portion of said brush part and communicating at its outer end with said annular space.

* * * * *